(12) United States Patent
Deaton et al.

(10) Patent No.: US 7,034,053 B2
(45) Date of Patent: Apr. 25, 2006

(54) PHENETHANOLAMINE DERIVATIVES, COMPOSITIONS, AND THEIR USE AS AGONISTS AT ATYPICAL BETA-ADRENORECEPTORS

(75) Inventors: David N. Deaton, Durham, NC (US); Barry George Shearer, Durham, NC (US); David Edward Uehling, Durham, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 260 days.

(21) Appl. No.: 10/470,860

(22) PCT Filed: Dec. 17, 2001

(86) PCT No.: PCT/US01/49299

§ 371 (c)(1),
(2), (4) Date: Jul. 31, 2003

(87) PCT Pub. No.: WO02/060885

PCT Pub. Date: Aug. 8, 2002

(65) Prior Publication Data

US 2004/0106672 A1    Jun. 3, 2004

(30) Foreign Application Priority Data

Jan. 31, 2001  (GB) ................... 0102408

(51) Int. Cl.
*A61K 31/381*  (2006.01)
*A61K 31/34*   (2006.01)
*C07D 333/38*  (2006.01)
*C07D 333/22*  (2006.01)
*C07D 307/02*  (2006.01)

(52) U.S. Cl. .................. 514/448; 514/471; 549/71; 549/72; 549/73; 549/484; 549/486

(58) Field of Classification Search .............. 549/71, 549/72, 73, 484, 486; 514/448, 471, 438
See application file for complete search history.

(56) References Cited

FOREIGN PATENT DOCUMENTS

| EP | 0 455 006 A2 * | 6/1991 |
| EP | 0 565 317 | 10/1993 |
| WO | 95/33724 | 12/1995 |
| WO | 97/21665 | 6/1997 |
| WO | 99/65877 | 12/1999 |

OTHER PUBLICATIONS

Lezama, Edwin J., et al., "Pharmacological Study of Atypical-Adrenoceptors in Rat Esophageal Smooth Muscle," European Journal of Pharmacology, vol. 308, May 16, 1996, p0p. 69-80.

* cited by examiner

*Primary Examiner*—Taofiq Solola
*Assistant Examiner*—Ebenzer Sackey
(74) *Attorney, Agent, or Firm*—Amy H. Fix

(57) ABSTRACT

The present invention disclosed compounds of Formula I. The present invention also discloses beta-3 agonists of formula I and methods for treating beta-3 mediated diseases and condition using the compounds of formula I, in particular methods for treating diabetes or obesity.

11 Claims, No Drawings

PHENETHANOLAMINE DERIVATIVES, COMPOSITIONS, AND THEIR USE AS AGONISTS AT ATYPICAL BETA-ADRENORECEPTORS

This application is filed pursuant to 35 U.S.C. § 371 as a United States National Phase Application of International Application No. PCT/US01/49299 Dec. 17, 2001, which claims priority from 0102408.2 filed Jan. 31, 2001.

FIELD OF THE INVENTION

This invention relates to a new class of chemical compounds and to their use in medicine. In particular, the invention concerns novel phenethanolamine derivatives, methods for their preparation, pharmaceutical compositions containing them and their use as agonists at a typical beta-adrenoceptors (also known as beta-3-adrenoceptors).

BACKGROUND OF THE INVENTION

A typical beta-adrenoceptors belong to the family of adrenoceptors that mediate the physiological actions of the hormones adrenaline and noradrenaline. Such receptors have been described for example by J R S Arch et. al., *Nature*, 309, 163–165 (1984); C Wilson et. al., *Eur. J. Pharmacol.*, 100, 309–319 (1984); L J Emorine et. al., *Science*, 245, 1118–1121 (1989); and A. Bianchetti et. al. *Br. J. Pharmacol.*, 100, 831–839 (1990).

Phenethanolamine derivatives having activity at a typical beta-adrenoceptors are disclosed in, for example, European Patent Applications EP-A-0455006 and EP-A-0543662.

Sub-types of the adrenoceptors, $\alpha_1$-, $\alpha_2$-, $\beta_1$-, $\beta_2$- and $\beta_3$-(atypical) can be identified on the basis of their pharmacological properties and physiological effects. Chemical agents that stimulate or block these receptors (but not $\beta_3$) are widely used in clinical medicine. More recently, emphasis has been placed upon specific receptor selectivity in order to reduce side effects caused, in part, by interactions with other receptors.

Atypical beta-adrenoceptors are known to occur in adipose tissue and the gastrointestinal tract. Atypical beta-adrenoceptor agonists have been found to be particularly useful as thermogenic anti-obesity agents and as anti-diabetic agents. Compounds having atypical beta-adrenoceptor agonist activity have also been described as being useful in the treatment of hyperglycaemia, as animal growth promoters, as blood platelet aggregation inhibitors, as positive inotropic agents and as antiatherosclerotic agents, and as being useful in the treatment of glaucoma.

SUMMARY OF THE INVENTION

The invention therefore provides, in a first aspect, compounds of formula (I) and pharmaceutically acceptable derivatives thereof:

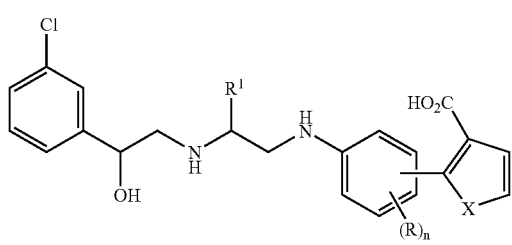

(I)

wherein X is oxygen or sulfur, and where the heterocycle containing X is substituted meta or para to the depicted NH;
$R^1$ is hydrogen or $C_{1-6}$alkyl;
R represents substituents selected from $C_{1-6}$ alkyl, halogen, trifluoromethyl and $C_{1-6}$alkoxy; and
n represents an integer from 0–4.

Preferably the compounds of this invention are agonists for human beta-3 adrenoceptor ("$\beta_3$"). More preferably, the compounds of this invention are selective agonists for $\beta_3$.

In another aspect, the present invention provides a pharmaceutical formulation comprising a compound of the invention. Preferred pharmaceutical compositions further comprise a pharmaceutically acceptable carrier.

In another aspect, the present invention provides a method for the prevention or treatment of clinical conditions or diseases susceptible to amelioration by administration of an a typical beta-adrenoceptor agonist, comprising administration of an effective amount of a compound or composition of this invention.

In a further aspect, the present invention provides the use of a compound of formula (I), or a pharmaceutically acceptable derivative thereof, in the manufacture of a medicament for the treatment of conditions or diseases susceptible to amelioration by administration of an a typical beta-adrenoceptor agonist.

DETAILED DESCRIPTION OF THE INVENTION

As used herein, the terms 'alkyl' and "alkoxy" mean a straight or branched alkyl group or alkoxy group respectively, containing the indicated number of carbon atoms. For example, $C_{1-6}$alkyl means a straight or branched alkyl containing at least 1 and at most 6 carbon atoms.

Preferably the heterocycle containing X is substituted meta to the depicted NH.

Preferably $R^1$ is hydrogen or methyl. When $R^1$ is other than hydrogen, then preferably the stereochemisty around the carbon to which $R^1$ is bonded is R.

Preferably R is chlorine, fluorine, or $CF_3$.

Preferably n is 0, 1, or 2. Most preferably n is 0.

Preferably the stereochemisty around the carbon to which the depicted OH is bonded is R.

It will be appreciated that the above compounds of Formula (I) may contain optically active centers. The individual, isolated isomers and mixtures thereof, including racemates, are all within the scope of the present invention. Typically, where $R^1$ is methyl, mixtures of diastereomers of compounds of Formula (I) may be obtained, which are enriched with greater than or equal to 80% by weight of one diastereomer.

Suitable compounds of formula (I) of the invention include:
2-(3-{2R-[2-(3-Chlorophenyl)-2R-hydroxyl-ethylamino]propylamino}phenyl)furan-3-carboxylic acid;
2-(3-{[2-(3-Chlorophenyl)-2R-hydroxyl-ethylamino]ethylamino}phenyl)furan-3-carboxylic acid;
2-(4-{2R-[2-(3-Chlorophenyl)-2R-hydroxyl-ethylamino]propylamino}phenyl)furan-3-carboxylic acid;
2-(3-{2R-[2-(3-Chlorophenyl)-2R-hydroxyl-ethylamino]propylamino}phenyl)thiophene-3-carboxylic acid;
2-(3-{[2-(3-Chlorophenyl)-2R-hydroxyl-ethylamino]ethylamino}phenyl)thiophene-3-carboxylic acid;
2-(4-{2R-[2-(3-Chlorophenyl)-2R-hydroxyl-ethylamino]propylamino}phenyl)thiophene-3-carboxylic acid; and pharmaceutically acceptable derivatives thereof.

Particularly preferred compounds of the invention include:

2-(3-{[2-(3-Chlorophenyl)-2R-hydroxyl-ethylamino] ethylamino}phenyl)furan-3-carboxylic acid;

2-(3-{[2-(3-Chlorophenyl)-2R-hydroxyl-ethylamino] ethylamino}phenyl)thiophene-3-carboxylic acid; and pharmaceutically acceptable derivatives thereof.

By "a pharmaceutically acceptable derivative" is meant any pharmaceutically acceptable salt, ester, or salt of such ester, of a compound of formula (I) or any other compound which, upon administration to the recipient, is capable of providing (directly or indirectly) a compound of formula (I) or an active metabolite or residue thereof.

It will be appreciated by those skilled in the art that the compounds of formula (I) may be modified to provide pharmaceutically acceptable derivatives thereof at any of the functional groups in the compounds of formula (I). Of particular interest as such derivatives are compounds modified at the carboxyl function, hydroxyl functions or at amino groups.

It will be appreciated by those skilled in the art that the pharmaceutically acceptable derivatives of the compounds of formula (I) may be derivatised at more than one position.

Preferred pharmaceutically acceptable derivatives of the compounds of formula (I) are pharmaceutically acceptable salts thereof.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable may be useful in the preparation of salts useful as intermediates in obtaining compounds of the invention and their pharmaceutically acceptable acid addition salts.

Salts derived from appropriate bases include alkali metal (e.g. sodium), alkaline earth metal (e.g. magnesium), ammonium and $NR_4^+$ (where R is $C_{1-4}$alkyl) salts.

The compounds of formula (I) and their pharmaceutically acceptable derivatives act as agonists at a typical beta-adrenoceptors and as such are useful in the treatment of clinical conditions susceptible to amelioration by administration of an a typical beta-adrenoceptor agonist. Such conditions include hyperglycaemia, obesity, hyperlipemia, irritable bowel syndrome and its associated pain, motility dysfunction, excessive gastrointestinal secretion, non-specific diarrhoea, neurogenic inflammation, regulation of intraocular pressure, triglyceridemia, diabetes, e.g. non-insulin-dependent diabetes mellitus (NIDDM or Type 2), such as obese NIDDM and non-obese NIDDM, diabetic complications such as retinopathy, nephropathy, neuropathy, cataracts, coronary heart diseases and arteriosclerosis, osteoporosis; and gastrointestinal disorders, particularly inflammatory gastrointestinal disorders. They are also of use in increasing the high-density-lipoprotein (HDL) cholesterol concentration and decreasing the triglyceride concentration in blood serum, especially human blood serum, and are therefore of potential use in the treatment and/or prophylaxis of atherosclerosis. They also may be useful for the treatment of hyperinsulinaemia, depression, muscle wasting, and urinary incontinence. References in this specification to treatment include prophylactic treatment as well as the alleviation of symptoms.

In a further aspect, the invention provides the use of a compound of general Formula (I) or a pharmaceutically acceptable salt or solvate thereof, for the manufacture of a medicament for the treatment of a condition susceptible of amelioration by an a typical beta-adrenoceptor agonist.

While it is possible that, for use in therapy, a compound of the invention may be administered as the raw chemical it is preferable to present the active ingredient as a pharmaceutical formulation. The invention thus further provides a pharmaceutical formulation comprising a compound of Formula (I) or a pharmaceutically acceptable derivative thereof together with one or more pharmaceutically acceptable carriers thereof and, optionally, other therapeutic and/or prophylactic ingredients. The carrier(s) or excipient(s) must be "acceptable" in the sense of being compatible with the other ingredients of the formulation and not deleterious to the recipient thereof.

The compounds for use according to the present invention may be formulated for oral, buccal, parenteral, rectal or transdermal administration or in a form suitable for administration by inhalation or insulation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

The compounds according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins, or as sparingly soluble derivatives, for example, as a sparingly soluble salt.

Suitable therapeutic ingredients which may be formulated with compounds of the invention, together with one or more pharmaceutical carriers or excipients, include ingredients which may be used in the same clinical conditions as those listed herein for atypical beta-adrenoceptor agonists. Such ingredients may include, for example, PPAR-gamma agonists.

A proposed dose of the compounds according to the present invention for administration to a human (of approximately 70 kg body weight) is 0.1 mg to 1 g, preferably to 1 mg to 100 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may be prepared by any of the processes known in the art for the preparation of similar compounds. For example, according to a first process wherein X, $R^1$, and R are as defined as for formula (I), compounds of formula (I) may be prepared by reaction of compounds of formula (II)

(III)

(II) and (III)
where $P^1$ and $P^2$ are suitable protecting groups for oxygen and nitrogen groups respectively and $R^2$ is lower alkyl or H, in the presence of a reducing agent, followed by deprotection of any protecting groups present.

Compounds of formula (II) are described in PCT publication number WO95/33724 or may be prepared by standard methods.

In an alternative process, a compound of formula (I) may be prepared by hydrolysis of a compound of formula (IV) or a pharmaceutically acceptable version thereof:

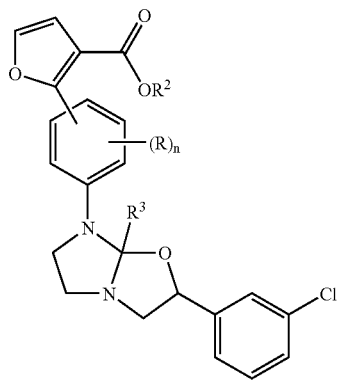

(IV)

wherein R and $R^1$ are as defined in formulas (II) and (III), $R^2$ is lower alkyl and $R^3$ represents $C_{1-6}$ alkyl or aryl optionally substituted by hydrogen, $C_{1-6}$ alkyl or halogen; followed by the step of hydrolysing the ester group —$CO_2R^2$ to produce a compound of formula (I), wherein the furan ring is substituted by a —$CO_2H$ group.

Preferably, hydrolysis of a compound of formula (IV) to form a compound of Formula (I) is carried out by reflux in the presence of an aqueous solution of a group 1 or group 2 metal hydroxide, e.g. NaOH or KOH, and preferably an alkanol, e.g. MeOH, for at least 4 h. The step of hydrolysing the ester group —$CO_2R^2$ to produce a compound of formula (IA), wherein $R^4$ is substituted by a —$CO_2H$ group can be carried out by a further hydrolysis step under standard hydrolysis conditions as would be apparent to a skilled person.

A compound of formula (IV) may be prepared by reacting a compound of formula (V) with a compound of formula (VI):

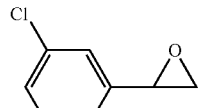

(V)

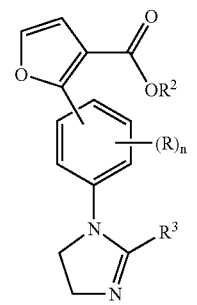

(VI)

at elevated temperature and pressure, optionally in the presence of one or more of: $C_{3-6}$alkanols, acetonitrile, N-methyl-pyrrolidinone (NMP), isobutylacetate, isopropylacetate, dimethylformamide (DMF), toluene, xylene or dimethylacetamide (DMA); preferably toluene and/or xylene. The temperature for the reaction is suitably 100° C. or greater, preferably 100–150° C., more preferably 100–120° C.

The reaction of a compound of formula (V) with a compound of formula (VI) to form a compound of formula (IV) and the subsequent conversion of a compound of formula (IV) to a compound of formula (I) may be carried out separately or in situ. The reaction is preferably carried out in situ.

A compound of formula (VI) may be prepared from a compound of formula (VII):

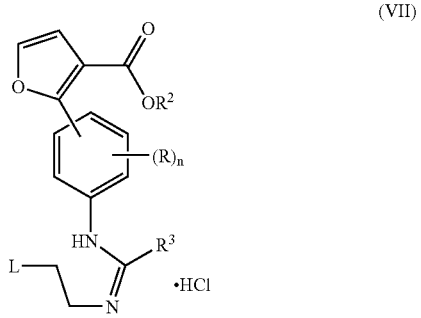

(VII)

wherein L represents a leaving group such as a halogen atom (e.g. chlorine), by cyclisation in the presence of a solvent selected from: dichloromethane (DCM), EtOAc, toluene and/or xylene, and a base selected from: $Na_2CO_3$, NaOH, anhydrous $Et_3N$ and/or an amine, e.g. aqueous $NH_3$. Preferably the solvent is DCM. Preferably the base is aqueous $NH_3$.

Compounds of Formula (VII) may be prepared from compounds of Formula (III) using any suitable method for the preparation of amidines. For example, by condensation of a compound of Formula (VIII) wherein L represents

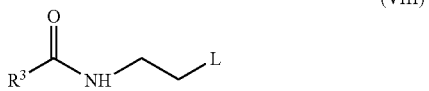

(VIII)

a leaving group as previously defined, in the presence of a solvent selected from: DCM, toluene, EtOAc, or $CH_3CN$, and $PCl_5$ or $POCl_3$. Preferably the solvent is EtOAc. Preferably $PCl_5$ is present.

A compound of formula (III) may be prepared by reaction of a compound of formula (IX)

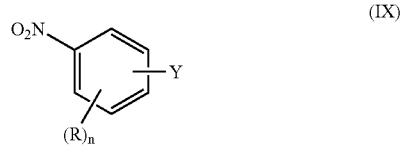

(IX)

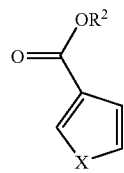

(X)

where Y represents the diazonium salt $N_2^+$, with a suitable 5-membered heterocyclic ring of formula (X), followed by reduction of the nitro group using standard methods. Suitable compounds of formula (X) are known or are prepared by standard methods. For example, where X is oxygen, thus forming a furan group, a compound of formula (III) may be prepared directly by reaction of a compound of formula (IX) where Y represents the diazonium salt $N_2^+$ with a furan of formula (X), followed by reduction with standard methods. A compound of formula (IX) where Y represents the diazonium salt $N_2^+$ may in turn be prepared from a compound of formula (IX) where $Y=NH_2$ by standard methods known in the literature. Alternatively, a compound of formula (III) may be prepared from the reaction of a compound of formula (IX) where Y=Br, I or triflate with a furan of formula (X) in the presence of a suitable palladium catalyst and a suitable base followed by reduction of the nitro group under standard conditions. Suitable palladium catalysts include, but are not limited to, tetrakis(triphenylphosphine) palladium(0). Suitable bases include, but are not limited to KOAc. Use of the palladium catalyst $Pd(PPh_3)_4$ in the presence of the base KOAc is preferred.

Compounds of formula (IX) are known compounds or may be prepared by processes well known in the art.

Suitable reducing agents of use in the reactions include hydrogen in the presence of a catalyst, such as a noble metal catalyst, for example palladium, platinum or platinum oxide, Raney-nickel or hydride reducing agents such as borohydrides, for example sodium borohydride sodium triacetoxyborohydride or sodium cyanoborohydride. Suitable reaction conditions will be readily apparent to those skilled in the art and are further illustrated by the accompanying examples.

The protecting groups used in the preparation of compounds of formula (I) may be used in conventional manner. See for example 'Protective Groups in Organic Chemistry' Ed. J. F. W. McOmie (Plenum Press 1973) or 'Protective Groups in Organic Synthesis' by Theodora W Greene and P M G Wuts (John Wiley and Sons 1991).

Conventional amino protecting groups may include for example aralkyl groups, such as benzyl, diphenylmethyl or triphenylmethyl groups; and acyl groups such as N-benzyloxycarbonyl or t-butoxycarbonyl.

Conventional oxygen protecting groups may include for example alky silyl groups, such as trimethylsilyl, or tert-butyldimethylsilyl; alkyl ethers such as tetrahydropyranyl, or tert-butyl; esters such as acetate.

Removal of any protecting groups present may be achieved by conventional procedures.

Atypical beta-adrenoceptor agonists are compounds, which demonstrate a pharmacological response mediated at atypical beta-adrenoceptors. This activity has been measured as the ability to stimulate lipolysis by rat adipocytes at sub-micromolar concentrations, in a response that is resistant to blockade by standard beta-adrenoceptor blocking drugs such as propranolol.

Another useful means of identifying an a typical beta-adrenoceptor agonist involves the measurement of agonist activity at a typical beta-adrenoceptors in the rat isolated lower oesophagus. Typically in this assay, a compound of general Formula (I) for use according to the present invention has an equipotent molar ratio (EPMR) relevant to isoprenaline of less than 30. The rat oesophagus assay is based upon that described by Ford et. al., Br. J. Pharmacol., 105(suppl.), 235P, 1992. The relative potency of each test compound (EPMR) is compared to isoprenaline as follows:

$$EPMR = \frac{EC50 \text{ agonist}}{EC50 \text{ isoprenaline}}$$

wherein $EC_{50}$ is the molar concentration of agonist which produces 50% of the maximum possible response for that agonist.

A particularly useful method for determining agonist activity at human a typical beta-adrenoceptors involves the use of Chinese hamster ovarian (CHO) cells transfected with the human beta-3-adrenoceptor according to Method 1. The cell lines may also be transfected with human beta-1- and beta-2-adrenoceptor in a similar manner to provide a method of determining the selectivity of the compounds of the invention at the three receptors.

Method 1—Cell Culture

General cell culture guidelines are observed (Fershney, R. A. (1987) Culture of animal cells: A manual of basic technique. Wiley-Liss, Inc., N.Y.). A standard cell culture incubator is used (37° C., 5% CO2 in air, 95% relative humidity). H $\beta_3$CHO cells are grown in DMEM/F12 (with pyroxidine-HCl, 15 mM HEPES, L-glutamine), supplanted with 10% heat-inactivated FBS, 500 µg/ml G418, 2 mM L-glutamine, 100 units penicillin G and 100 µg streptomycin sulfate. One confluent flask of cells is trypsinised and resuspended in the above medium at a concentration of 30–40,000 cells/100 µl and plated into 96-well flat bottom plates. The cells are then used for assay within 18–24 hours.

The medium is aspirated from each well, and replaced with 180 µl DMEM/F12 with 500 mM IBMX. Antagonists, if required, are added at this stage. The plate is then placed back in the incubator for 30 min. Drugs are then added to the wells (20 µl, 100× required final concentration) for 60 min. Responses were determined by measuring cAMP levels of a 20 ul sample of extracellular media using a scintillation proximity based radio-immunoassay (NEN Flashplates).

CHO-6CRE-luciferase cell lines which stably express $h\beta_3$ receptors are seeded at 30,000 cells/well for 24 hr in DMEM/F12 containing 10% FBS. Media is removed from the cells and replaced with DMEM/F12 buffer (180 µl) containing 300 mM IBMX and 1 mM ascorbic acid for 30 min prior to addition of compound. Vehicle or agonist (20 µl) is added and incubated at 37° C. for 60 minutes. At the end of the incubation period, samples of extracellular media are removed for direct assay in cAMP Flashplates (NEN).

As used herein, a compound is considered to be an agonist for $h\beta_3$ if the compound stimulates the accumulation of extracellular cAMP with CHO-6CRE-luciferase cells expressing $h\beta_3$. The compounds of this invention have an $EC_{50}$ of at most 10 nM at $h\beta_3$. The relative potency of a $h_3$ agonist may be compared to its potency for stimulating the accumulation of extracellular cAMP with CHO- 6CRE-luciferase cells expressing $h\beta_2$ and $h\beta_1$. The compounds of this invention are at least 100 times more potent at $h\beta_3$ than at $h\beta_2$ or $h\beta_1$.

The invention is further illustrated by the following intermediates and examples. All temperatures are in degrees centigrade. Chromatography was carried out on silica (Merck 9385) unless otherwise stated. HPLC characterization systems are labeled as follows:

System 1: (C18), using a 30–80% acetonitrile-water with 0.1% trifluoroacetic acid gradient mobile phase with detection by absorbance at 254 nM.

System 2: (C18), using 1:4 acetonitrile-water containing trifluoroacetic acid (0.1%) and triethylamine (0.1%) mobile phase with detection by absorbance at 254 nM.

System 3: (C18), using 30–100% acetonitrile-water containing trifluoroacetic acid (0.1%) and triethylamine (0.1%) mobile phase with detection by absorbance at 254 nM.

System 4: (C18), using 1:1 acetonitrile-water containing trifluoroacetic acid (0.1%) mobile phase with detection by absorbance at 254 nM HPLC retention times are expressed in minutes as $t_R$.

Intermediate 1

2-[3-(2R-{tert-Butoxycarbonyl-[2R-(tert-butyldimethylsilanoxy)-2-(3-chlorophenyl)ethyl]-amino}propylamino)phenyl]furan-3-carboxylic acid methyl ester.

A solution of 2-(3-aminophenyl)furan-3-carboxylic acid methyl ester (0.31 g) and {2R-(tert-butoxycarbonyl)-[2R-(tert-butyldimethylsilanoxy)-2-(3-chlorophenyl)ethyl]amino}propionaldehyde (0.63 g) in dichloromethane (9 mL) containing acetic acid (0.03 mL) was stirred at room temperature for 30 min. The reaction mixture was cooled to 0° C. and sodium triacetoxyborohydride (0.30 g) was added. The mixture was stirred at room temperature for 18 h, washed with aqueous sodium bicarbonate solution, dried over magnesium sulfate, and concentrat d under reduced pressure. The residue was chromatographed on silica eluting with hexanes: ethyl acetate (9:1) to give the title compound as a yellow solid (0.523 g). $C_{34}H_{47}N_2O_6ClSi$: M+Na 665

Similarly Prepared Were:

Intermediate 2

2-[3-{tert-Butoxycarbonyl-[2R-(tert-butyldimethylsilanoxy)-2-(3-chlorophenyl)ethyl]-amino}ethylamino)phenyl]furan-3-carboxylic acid methyl ester as a colorless gum (1.15 g), $C_{33}H_{45}N_2O_6ClSi$: MH+ 629, from 2-(3-aminophenyl)furan-3-carboxylic acid methyl ester (742 mg) and {(tert-butoxycarbonyl)-[2R-(tert-butyl-dimethyl-silanyloxy)-2-(3-chloro-phenyl)-ethyl]-amino}acetaldehyde (1.17 g).

Intermediate 3

2-[4-(2R-{tert-Butoxycarbonyl-[2R-(tert-butyldimethylsilanoxy)-2-(3-chlorophenyl)ethyl]-amino}propylamino)phenyl]furan-3-carboxylic acid methyl ester as a brown oil (0.45 g), TLC hexane:ethyl acetate (1:1) $R_f$=0.65, from 2-(4-aminophenyl)furan-3-carboxylic acid methyl ester (0.22 g) and {2R-(tert-butoxycarbonyl)-[2R-(tert-butyldimethylsilanoxy)-2-(3-chlorophenyl)ethyl]amino}propionaldehyde (0.45 g).

Intermediate 4

2-[3-(2R-{tert-Butoxycarbonyl-[2R-(tert-butyldimethylsilanoxy)-2-(3-chlorophenyl)ethyl]amino}propylamino)phenyl]thiophene-3-carboxylic acid methyl ester as a yellow oil (0.383 g), TLC hexane:ethyl acetate (1:1) $R_f$=0.66, from 2-(3-aminophenyl)thiophene-3-carboxylic acid methyl ester (0.30 g) and {2R-(tert-butoxycarbonyl)-[2R-(tert-butyldimethylsilanoxy)-2-(3-chlorophenyl)ethyl]amino}propionaldehyde (0.56 g).

Intermediate 5

2-[3-{tert-Butoxycarbonyl-[2R-(tert-butyldimethylsilanoxy)-2-(3-chlorophenyl)ethyl]-amino}ethylamino)phenyl]thiophene-3-carboxylic acid methyl ester as a colorless gum (1.15 g). $C_{33}H_{45}N_2O_5ClSSi$: $MH^+$ 646, from 2-(3-aminophenyl)thiophene-3-carboxylic acid methyl ester (795 mg) and {(tert-butoxycarbonyl)[2R-(tert-butyl-dimethyl-silanyloxy)-2-(3-chloro-phenyl)-ethyl]-amino}-acetaldehyde (1.17 g).

Intermediate 6

2-[4-(2R-{tert-Butoxycarbonyl-[2R-(tert-butyldimethylsilanoxy)2-(3-chlorophenyl)ethyl]amino}propylamino)phenyl]thiophene-3-carboxylic acid methyl ester as a yellow oil (0.155 g), $C_{34}H_{47}N_2O_5ClSSi$: $MH^+$ 659, from 2-(4-aminophenyl)thiophene-3-carboxylic acid methyl ester (0.17 g) and {2R-(tert-butoxycarbonyl)-[2R-(tert-butyldimethylsilanoxy)-2-(3-chlorophenyl)ethyl]amino}propionaldehyde (0.32 g).

Intermediate 7

2-(3-Nitrophenyl)furan-3-carboxylic acid

A solution of 3-nitroaniline (8.28 g) in concentrated hydrochloric acid (20 mL) was treated with sodium nitrite (4.2 g) in water (20 mL) at 0° C. The mixture was stirred for 10 min, and then filtered. To the filtrate was added 3-furancarboxylic acid (6.05 g) in acetone (10 mL), followed by a solution of cupric chloride (2.4 g) in water (8 mL). The mixture was left to stand at room temperature for two days, poured into water (200 mL), and stirred for two hours. The resulting solid was dissolved in 10% sodium bicarbonate solution, and triturated with ethyl aceate. The resulting aqueous solution was acidified with 1N hydrochloric acid to precipitate a solid. Recrystallization of the solid from benzene gave the title compound as a brown solid (3.57 g). $C_{11}H_7NO_5$: $MH^+$ 232

Similarly Prepared Were:

Intermediate 8

2-(4-Nitrophenyl)furan-3-carboxylic acid as a tan solid (1.52 g), n.m.r. (DMSO-$d_6$) δ values include 6.91 (s, 1H), 7.96 (s, 1H), 8.27 (dd, 4H), 13.09 (bs, 1H), from 4-nitroaniline (4.14 g) and 3-furancarboxylic acid (3.03 g).

Intermediate 9

2-(3-Nitrophenyl)thiophene-3-carboxylic acid as a tan solid (0.45 g), $C_{11}H_7NO_4S$: $MH^-$ 248, from 3-nitroaniline (4.14 g) and 3-thiophenecarboxylic acid (3.46 g).

Intermediate 10

2-(4-Nitrophenyl)thiophene-3-carboxylic acid as a tan solid (2.83 g), $C_{11}H_7NO_4S$: $MH^-$ 248, from 4-nitroaniline (4.14 g) and 3-thiophenecarboxylic acid (3.46 g).

Intermediate 11

2-(3-Nitrophenyl)furan-3-carboxylic acid methyl ester

A solution of 2-(3-nitrophenyl)furan-3-carboxylic acid (1.2 g) in methanol (200 mL) containing concentrated sulfuric acid (5 drops) was heated under reflux for 18 h. The reaction solution was evaporated to dryness under reduced pressure to give the title compound as a yellow solid (0.66 g). m.p.=93–94° C.

Similarly Prepared Were:

Intermediate 12

2-(4-Nitrophenyl)furan-3-carboxylic acid methyl ester as a yellow solid (1.15 g), m.p.=113–114° C., from 2-(4-nitrophenyl)furan-3-carboxylic acid (0.52 g).

Intermediate 13

2-(3-Nitrophenyl)thiophene-3-carboxylic acid methyl ester as a white solid (0.31 g), $C_{12}H_9NO_4S$: $MH^-$ 262, from 2-(3-nitrophenyl)thiophene-3-carboxylic acid (0.45 g).

Intermediate 14

2-(4-Nitrophenyl)thiophene-3-carboxylic acid methyl ester as a white solid (1.0 g), n.m.r. (DMSO-$d_6$) δ values include 3.78 (s, 3H), 7.43 (d, 1H), 7.64 (m, 1H), 7.72 (m, 2H), 8.21 (d, 1H), 8.33 (m, 1H), from 2-(4-nitrophenyl)thiophene-3-carboxylic acid (1.5 g).

Intermediate 15

2-(3-Aminophenyl)furan-3-carboxylic acid methyl ester

A solution of 2-(3-nitrophenyl)furan-3-carboxylic acid methyl ester (1.0 g) in methanol (60 mL) containing 10% palladium on carbon (2.9 g) was stirred under 1 atmosphere of hydrogen for 1 h. The reaction mixture was then filtered through Celite. Removal of the solvent at reduced pressure gave the title compound as a yellow solid (0.75 g). $C_{12}H_{11}NO_3$: M+Na+ 240

Similarly Prepared Were:

Intermediate 16

2-(4-Aminophenyl)furan-3-carboxylic acid methyl ester as a yellow solid (1.0 g), Assay Found: C 66.19; H 5.17; N 6.33%, $C_{12}H_{11}NO_3$ requires C 66.35; H 5.10; N 6.45%, from 2-(4-nitrophenyl)furan-3-carboxylic acid methyl ester (1.0 g).

Intermediate 17

2-(3-Aminophenyl)thiophene-3-carboxylic acid methyl ester as a brown oil (0.30 g), $C_{12}H_{11}NO_2S$: M+Na+ 255, from 2-(3-nitrophenyl)thiophene-3-carboxylic acid methyl ester (0.30 g).

Intermediate 18

2-(4-Aminophenyl)thiophene-3-carboxylic acid methyl ester as a brown oil (0.17 g), $C_{12}H_{11}NO_2S$: MH$^+$ 234, from 2-(4-nitrophenyl)thiophene-3-carboxylic acid methyl ester (0.70 g).

Intermediate 19

2-(3-{2R-[2-(3-Chlorophenyl)-2R-hydroxyl-ethylamino]propylamino}phenyl)furan-3-carboxylic acid methyl ester 2-[3-(2R-{tert-Butoxycarbonyl-[2R-(tert-butyldimethylsilanoxy)-2-(3-chlorophenyl)ethyl]amino}propylamino)phenyl]furan-3-carboxylic acid methyl ester (0.523 g) was dissolved in 4N hydrochloric acid in dioxane (5.0 mL), stirred at room temperature for 1 h and then diluted with diethyl ether (10 mL) to separate an oil. The oil was chromatographed on silica and eluting with ethyl acetate:methanol (9:1) to give the title compound as a red oil (0.19 g). $C_{23}H_{25}N_2O_4Cl$: MH$^+$ 429

Intermediate 20

2-(3-{2R-[2-(3-Chlorophenyl)-2R-hydroxyl-ethylamino]propylamino}phenyl)furan-3-carboxylic acid methyl ester hydrochloride as a white solid (613 mg), $C_{22}H_{23}N_2O_4Cl$: MH$^+$ 415, from 2-[3-{tert-butoxycarbonyl-[2R-(tert-butyldimethylsilanoxy)-2-(3-chlorophenyl)ethyl]-amino}ethylamino)phenyl]thiophene-3-carboxylic acid methyl ester (1.15 g).

Similarly Prepared Were:

Intermediate 21

2-(4-{2R-[2-(3-Chlorophenyl)-2R-hydroxyl-ethylamino]propylamino}phenyl)furan-3-carboxylic acid methyl ester as a brown oil (0.19 g), TLC ethyl acetate: methanol (8:2) R$_f$=0.27, from 2-[4-(2R-{tert-butoxycarbonyl-[2R-(tert-butyldimethylsilanoxy)-2-(3-chlorophenyl)ethyl]-amino}propylamino)phenyl]furan-3-carboxylic acid methyl ester (0.45 g).

Intermediate 22

2-(3-{2R-[2-(3-Chlorophenyl)-2R-hydroxyl-ethylamino]propylamino}phenyl)thiophene-3-carboxylic acid methyl ester as an range oil (0.086 g), $C_{23}H_{25}N_2O_3ClS$: MH$^+$ 445, from 2-[3-(2R-{tert-butoxycarbonyl-[2R-(tert-butyldimethylsilanoxy)-2-(3-chlorophenyl)ethyl]amino}propylamino)phenyl]thiophene-3-carboxylic acid methyl ester (0.383 g).

Intermediate 23

2-(3-{2R-[2-(3-Chlorophenyl)-2R-hydroxyl-ethylamino]propylamino}phenyl)thiophene-3-carboxylic acid methyl ester hydrochloride as a tan foam (1.15 g), $C_{22}H_{23}N_2O_3ClS$: MH$^+$ 431, from 2-[3-{tert-butoxycarbonyl-[2R-(tert-butyldimethylsilanoxy)-2-(3-chlorophenyl)ethyl]-amino}ethylamino)phenyl]thiophene-3-carboxylic acid methyl ester (1.65 g).

Intermediate 24

2-(4-{2R-[2-(3-Chlorophenyl)-2R-hydroxyl-ethylamino]propylamino}phenyl)thiophene-3-carboxylic acid methyl ester as an orange oil (0.060 g), $C_{23}H_{25}N_2O_3ClS$: MH$^+$ 445, from 2-[4-(2R-{tert-butoxycarbonyl-[2R-(tert-butyldimethylsilanoxy)-2-(3-chlorophenyl)ethyl]amino}propylamino)phenyl]thiophene-3-carboxylic acid methyl ester (0.155 g).

Intermediate 25

Methyl 2-(3-{2R-[2-(3-chlorophenyl)-2R-hydroxyl-ethylamino]propylamino}phenyl)furan-3-carboxylate as a white foam (992 mg), $C_{34}H_{47}N_2O_6SiCl$: [MH$^+$] 643, from 2-(3-aminophenyl)furan-3-carboxylic acid methyl ester (700 mg) and {2R-(tert-butoxycarbonyl)-[2R-(tert-butyldimethylsilanoxy)-2-(3-chlorophenyl)ethyl]amino}propionaldehyde (1.26 g).

Intermediate 26

Methyl 2-(3-{2R-[2-(3-chlorophenyl)-2R-hydroxyl-ethylamino]-N-ethylpropylamino}phenyl)furan-3-carboxylate as a white foam (331 mg), $C_{35}H_{51}N_2O_6SiCl$: [MH$^+$] 671, from methyl 2-(3-{2R-[2-(3-chlorophenyl)-2R-hydroxyethylamino]propylamino}phenyl)furan-3-carboxylate (429 mg) and acetaldehyde (47 mg).

Intermediate 27

Ethyl 2-(3-aminophenyl)-3-furoate hydrochloride

To a stirred solution of 1-bromo-3-nitrobenzene (50 g) and ethyl 3-furoate (48.6 g) in toluene (500 mL) were added potassium acetate (36.4 g) and tetrakis(triphenylphosphine)palladium(0) (14.3 g). The mixture was heated at reflux for 66 hours, cooled to room temperature, and filtered through Celite (50 g). The filtercake was rinsed with ethyl acetate (2×200 mL). The combined filtrate/rinse was concentrated to an oil. Methanol (500 mL) and 10% palladium on carbon (50% wet paste, 3.2 g) were added. The mixture was stirred under an atmosphere of hydrogen until uptake ceased. The mixture was filtered through Celite (50 g), and the filtercake was rinsed with ethyl acetate (200 mL). The combined filtrate/rinse was concentrated to an oil, and ethyl acetate (250 mL) was added. The solution was washed with water (100 mL). The organic phase was dried over sodium sulfate, filtered, and concentrated to an oil. Dichloromethane (50 mL) was added, and the resulting solution was filtered through a silica gel plug (100 g). The plug was rinsed with dichloromethane (2500 mL) to extract all ethyl 2-(3-aminophenyl)-3-furoate hydrochloride. The combined filtrate/rinse was concentrated to an oil, and methyl tert-butyl ether (250 mL) was added. To this stirred solution was slowly added 4.0 M HCl in dioxane (93 mL). After aging for 15 minutes at 0–5° C., the precipitate was collected by filtration, washed with methyl tert-butyl ether (2×100 mL), and dried in vacuo at 45–50° C. to yield 46.8 g (71% th) of the title compound as a beige solid. 1H NMR (300 MHz, d6-DMSO) δ:7.90 (d, 1H), 7.78 (m, 2H), 7.51 (t, 1H), 7.30 (d, 1H), 4.25 (q, 2H), 1.26 (t, 3H).

Intermediate 28

Ethyl 2-[3-(2-methyl-4,5-dihydro-1H-imidazol-1-yl)phenyl]-3-furoate

N-(2-chloroethyl)acetamide (1.21 g) in ethyl acetate (10 mL) was added over 10 min to a stirred suspension of phosphorus pentachloride (2.08 g) in ethyl acetate (2 mL) at 0° C. under nitrogen to give a clear pale straw solution. After 45 min at 0° C. toluene (12 mL) was added, and ethyl 2-(3-aminophenyl)-3-furoate hydrochloride (1.78 g) was added in one portion into the above solution at 0–5° C. The mixture was stirred at 0–5° C. for 10 min and then allowed to warm up to 20° C. After 2 h formation of the amidine is essentially complete (HPLC ethyl 2-(3-aminophenyl)-3-furoate hydrochloride <2% @ 220 nm, a/a). The mixture was cooled to 0–5° C., crushed ice (18 g) was added over 20 min to destroy phosphorus oxychloride. Ammonium hydroxide (28%, 6.49 mL) was added at a rate that the internal temperature was kept below 25° C. (ca. 15 min). After 1 h at 20° C. additional ethyl acetate (12 mL) added to the above mixture, the organic layer was separated, washed with deionized water (2×12 mL), and concentrated under reduced pressure. The residue was dissolved in acetone (5 mL) and ethyl acetate (5 mL), and treated with oxalic acid (0.72 g) at 40° C. for 30 min. After aging at <20° C. for at least 12 h, the precipitate was collected by filtration, washed with acetone (2×0.5 vol), and dried in vacuo at 45–50° C. to yield 1.9 g (73%) of white solid. $^1$H NMR (400, $d_6$-DMSO) δ: 8.00 (s, 1H), 7.92–7.90 (m, 2H), 7.64–7.55 (m, 2H), 6.90 (d, 1H), 4.32 (t, 2H), 4.22 (q, 2H), 3.93 (t, 2H), 2.22 (s, 3H), 1.24 (t, 3H).

EXAMPLE 1

2-(3-{2R-[2-(3-Chlorophenyl)-2R-hydroxyl-ethylamino]propylamino}phenyl)furan-3-carboxylic acid To a solution of 2-(3-{2R-[2-(3-chlorophenyl)-2R-hydroxyl-ethylamino]propylamino}phenyl)furan-3-carboxylic acid methyl ester (0.19 g) in 3:1 methanol: water (5.5 mL) was added solid lithium hydroxide monohydrate (0.185 g). The solution was stirred at room temperature for 18 h and concentrated at reduced pressure. The residue was chromatographed on silica eluting with chloroform: methanol: conc. ammonium hydroxide (10:5:1) to give the title compound as a tan solid (0.067 g). m.p.=184–186° C., HPLC system 1: $t_R$ 11.19 min.

Similarly Prepared Were:

EXAMPLE 2

2-(3-{[2-(3-Chlorophenyl)-2R-hydroxyl-ethylamino]ethylamino}phenyl)furan-3-carboxylic acid as a white solid (317 mg), m.p.=250° C. (dec), $C_{21}H_{21}N_2O_4Cl$: [MH$^+$] 402. Assay Found C 62.65; H 5.21; N 6.91%, $C_{21}H_{21}N_2O_4Cl_1$ requires C 62.92; H 5.28; N 6.99%, from 2-(3-{2R-[2-(3-chlorophenyl)-2R-hydroxyl-ethylamino]propylamino}phenyl)furan-3-carboxylic acid methyl ester hydrochloride (613 mg).

In an alternative preparation, ammonium hydroxide (28%, 13 mL) was added over 10 min to a mixture of ethyl 2-[3-(2-methyl-4,5-dihydro-1H-imidazol-1-yl)phenyl]-3-furoate (13.0 g), deionized water (104 mL), and toluene (104 mL). After 30 min stirring, the organic layer was collected, washed with deionized water (26 mL), and concentrated to ca. 30 mL to remove traces of water azetropically. (R)-3-Chlorostyrene oxide (5.17 g) was added, and the resultant was heated under nitrogen at 110 C. for at least 14 h. The mixture was cooled to ca. 50° C. 1M Sodium hydroxide aqueous solution (77.8 mL) and methanol (39 mL) were added, and the apparatus was configured for distillation. After ca. 1 h, the homogeneous solution obtained was heated at reflux (ca. 4 h) until the hydrolysis was complete (HPLC acetate <2% @ 220 nm, a/a). The mixture was cooled to <50° C.

Methanol (26 mL) and 1M hydrochloric acid (78 mL) were heated to ca. 50° C. The reaction mixture from above was added over 20 min, and the resultant slurry was cooled to <20° C. and aged for a further 30 min. The product was collected by filtration, washed with deionized water (2×26 mL), and dried in vacuo at 50° C. to yield 12.7 g (95%) of the title compound as an off-white solid.

EXAMPLE 3

2-(4-{2R-[2-(3-Chlorophenyl)-2R-hydroxylethylamino]propylamino}phenyl)furan-3-carboxylic acid as a tan solid (0.059 g), HRMS $C_{22}H_{23}N_2O_4Cl$: MH$^+$ calc 415.1425, found 415.1412 Δ=1.3 mmu, HPLC system 1: $t_R$ 11.06 min., from 2-(4-{2R-[2-(3-chlorophenyl)-2R-hydroxylethylamino]propylaminophenyl}furan-3-carboxylic acid methyl ester (0.19 g).

EXAMPLE 4

2-(3-{2R-[2-(3-Chlorophenyl)-2R-hydroxyl-ethylamino]propylamino}phenyl)thiophene-3-carboxylic acid as a tan solid (0.088 g), HRMS $C_{22}H_{23}N_2O_3ClS$ MH$^+$ calc 431.1196, found 431.1180 Δ=1.6 mmu, HPLC system 1: $t_R$ 12.38 min., from 2-(3-{2R-[2-(3-chlorophenyl)-2R-hydroxyl-ethylamino]propylamino}phenyl)thiophene-3-carboxylic acid methyl ester (0.086 g).

EXAMPLE 5

2-(3-{[2-(3-Chlorophenyl)-2R-hydroxyl-ethylamino]ethylamino}phenyl)thiophene-3-carboxylic acid as a cream colored solid (296.8 mg), m.p.=275° C. (dec) $C_{21}H_{21}N_2O_3ClS$: [MH$^+$] 417. Assay Found C 60.47; H 5.04; N 6.67%, $C_{21}H_{21}N_2O_4Cl_1$ requires C 60.50; H 5.08; N 6.72%, from 2-(3-{2R-[2-(3-chlorophenyl)-2R-hydroxyl-ethylamino]propylamino}phenyl)thiophene-3-carboxylic acid methyl ester hydrochloride (1.15 g).

EXAMPLE 6

2-(4-{2R-[2-(3-Chlorophenyl)-2R-hydroxyl-ethylamino]propylamino}phenyl)thiophene-3-carboxylic acid as a tan solid (0.010 g), HRMS $C_{22}H_{23}N_2O_3ClS$ MH$^+$ calc 431.1196, found 431.1183 Δ=1.3 mmu, HPLC system 1: $t_R$ 12.03 min., from 2-(4-{2R-[2-(3-chlorophenyl)-2R-hydroxyl-ethylamino]propylamino}phenyl)thiophene-3-carboxylic acid methyl ester (0.060 g).

What is claimed is:

1. A compound of formula (I), or a pharmaceutically acceptable derivative thereof:

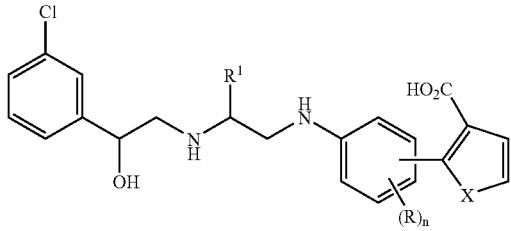

wherein X is oxygen or sulfur, and where the heterocycle containing X is substituted meta or para to the depicted NH;

$R^1$ is hydrogen or $C_{1-6}$alkyl;

R represents substituents selected from $C_{1-6}$ alkyl, halogen, trifluoromethyl, and $C_{1-6}$alkoxy; and n represents an integer from 0–4.

2. A compound of claim 1 wherein the heterocycle containing X is substituted meta to the depicted NH.

3. A compound of claim 1 wherein $R^1$ is hydrogen or methyl.

4. A compound of claim 1 wherein when $R^1$ is other than hydrogen, the stereochemisty around the carbon to which $R^1$ is bonded, is R.

5. A compound of claim 1 wherein R is chlorine, fluorine, or $CF_3$.

6. A compound of claim 1 wherein n is 0, 1, or 2.

7. A compound of claim 1 wherein n is 0.

8. A compound of claim 1 wherein the stereochemisty around the carbon to which the depicted OH is bonded, is R.

9. A compound of claim 1 wherein said compound is selected from the group consisting of 2-(3-{2R-[2-(3-Chlorophenyl)-2R-hydroxyl-ethylamino]propylamino}phenyl)furan-3-carboxylic acid;

2-(3-{[2-(3-Chlorophenyl)-2R-hydroxyl-ethylamino]ethylamino}phenyl)furan-3-carboxylic acid;

2-(4-{2R-[2-(3-Chlorophenyl)-2R-hydroxylethylamino]propylamino}phenyl)furan-3-carboxylic acid;

2-(3-{2R-[2-(3-Chlorophenyl)-2R-hydroxyl-ethylamino]propylamino}phenyl)thiophene-3-carboxylic acid;

2-(3-{[2-(3-Chlorophenyl)-2R-hydroxyl-ethylamino]ethylamino}phenyl)thiophene-3-carboxylic acid;

2-(4-{2R-[2-(3-Chlorophenyl)-2R-hydroxyl-ethylamino]propylamino}phenyl)thiophene-3-carboxylic acid;

and pharmaceutically acceptable derivatives thereof.

10. A compound of claim 1 wherein said compound is selected from the group consisting of 2-(3-{[2-(3-Chlorophenyl)-2R-hydroxyl-ethylamino]ethylamino}phenyl)furan-3-carboxylic acid;

2-(3-{[2-(3-Chlorophenyl)-2R-hydroxyl-ethylamino]ethylamino}phenyl)thiophene-3-carboxylic acid;

and pharmaceutically acceptable derivatives thereof.

11. A pharmaceutical formulation comprising a compound of claim 1 and one or more pharmaceutically acceptable carrier.

* * * * *